(12) United States Patent
Rossiter

(10) Patent No.: US 6,313,087 B1
(45) Date of Patent: Nov. 6, 2001

(54) PERFUMES COMPRISING 3-ALKYLCYCLOALKANOLS

(75) Inventor: Karen Jane Rossiter, Kent (GB)

(73) Assignee: Quest International BV, Maarden (NL)

(*) Notice: Subject to any disclaimer, the term of this patent is extended or adjusted under 35 U.S.C. 154(b) by 0 days.

(21) Appl. No.: 09/403,692

(22) PCT Filed: Apr. 22, 1998

(86) PCT No.: PCT/GB98/01166
§ 371 Date: Oct. 25, 1999
§ 102(e) Date: Oct. 25, 1999

(87) PCT Pub. No.: WO98/47842
PCT Pub. Date: Oct. 29, 1998

(30) Foreign Application Priority Data

Apr. 23, 1997 (EP) .................................................. 97302786
Mar. 30, 1998 (EP) .................................................. 98302421

(51) Int. Cl.[7] ....................................................... A61K 7/46
(52) U.S. Cl. ................ 512/25; 512/23; 512/22; 568/821; 568/822; 568/838; 510/101
(58) Field of Search .................. 512/25, 23, 22, 512/8; 568/821, 822, 838; 510/101

(56) References Cited

U.S. PATENT DOCUMENTS 3,769,330  10/1973  Nikawitz et al. .
4,400,545  8/1983  Willis et al. .
5,525,589  6/1996  Etzweiler et al. .

OTHER PUBLICATIONS

Downes, et al., "The Synthesis of Some Alkylated Cyclohexenones and Aromatic Compounds", Journal of the American Chemical Society, vol. 72, No. 8, Aug. 15, 1950, Washington, DC, US, pp. 3464–3467, XP002072412, see p. 3464, right–hand column, line 18–20.

*Primary Examiner*—Jill Warden
*Assistant Examiner*—Monique T. Cole
(74) *Attorney, Agent, or Firm*—Pillsbury Winthrop LLP

(57) ABSTRACT

Perfumes and perfumed products comprising 3-alkylcycloalkan-1-ols of formula (I), wherein $R_1$ represents hydrogen or a methyl, ethyl or propyl group; $R_2$, $R_4$ and $R_5$ independently represent hydrogen or a methyl group; $R_3$ represents a saturated hydrocarbon group with 4–8 carbon atoms, provided that the first carbon atom of this hydrocarbon group is not a tertiary carbon atom, and n represents the numbers 1, 2 and 3. The invention also concerns compounds of formula (I) wherein $R_1$ represents a methyl, ethyl or propyl group and $R_2$–$R_5$ are as outlined above.

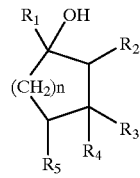

Formula I

16 Claims, No Drawings

PERFUMES COMPRISING 3-ALKYLCYCLOALKANOLS

This application is the national phase of international application PCT/GB98/01166 filed Apr. 22, 1998 which designated the U.S.

FIELD OF THE INVENTION

The invention relates to 3-alkyl-cyclopentan-1-ols, cyclohexan-1-ols and cycloheptan-1-ols, to their use as fragrance materials and to perfumes and perfumed products comprising these alcohols.

BACKGROUND TO THE INVENTION

In the perfumery art there is a continuous interest in new fragrance materials, on the one hand caused by a continuous need for compounds with a new odour character and on the other hand caused by the fact that many of the long Known materials have come under scrutiny lately because of certain undesirable properties. Thus, some well known fragrance materials have been criticized because of their potential instability in some applications. Some of these are well known floral fragrances, such as α-hexylcinnamaldehyde, 2-methyl-3-(p-tert-butylphenyl)propanal, 2-methyl-3-(p-isopropylphenyl)propanal, 3-(p-tert-butylphenyl)propanal and hydroxycitronellal.

Some alkyl substituted cyclohexanols are long known in perfumery. Thus, S. Arctander, Perfume and Flavor Chemicals mentions: 4-isopropyl-, 4-tert.butyl-, 4-tert.amyl-, 4-heptyl-, 4-ethyl- and 2-methyl-4-tert.amyl-cyclohexanol (monograph no's 2692, 433, 165, 1531, 1201 and 1749). The odour character of all five compounds is overridingly woody with camphoraceous, piney, vetiver and cedar notes, and often also dry with tarry or leathery odour notes. 2-Tert.butylcyclohexanol (monogr.no. 432) is also described as dry woody, camphoraceous and tarry.

Certain 4-isoamylcyclohexanols, particularly di-, tri- and tetra-methyl substituted ones are disclosed in U.S. Pat. No. 4,400,545 as fragrance materials with baisamic, woody, sweet, rooty, musty, earthy and leathery odours.

4-(C8-Alkyl)-cyclohexanols are disclosed in EP 0 005 196 as having an odour resembling that of 4-tert.butyl-cyclohexanol, but less strong. The most important compound is 4-(2,2,3,3tetramethylbutyl)cyclohexanol.

In Japanese patent application JP 02131405 (Hasegawa Koryo Co. Ltd) 2-, 3- and 4-alkylcycloalkanols and esters thereof are described as cockroach repellents. In passing it is stated that these compounds are used as fragrances, but for the alcohols this is not further substantiated than by referring to the Arctander monographs cited above, and no indication of odour character is given in this patent application.

In EP 0 053 979 alkyl substituted 3-(2-alkenyl) cyclopentanols are broadly disclosed with a wide variety of odour notes of the floral, fruity and woody type reminiscent of rose, muguet, bergamot, cucumber, hay-like, dry-woody, cedar or vetiver. The specific compounds shown are all unsubstituted 3-(2-alkenyl)cyclopentanols and 1,2,2-trimethyl-3-(2-alkenyl)cyclopentanols.

In U.S. Pat. No. 4,277,618 1-methyl-2-(C4alkyl) cyclohexanols (C4=sec.butyl or tert.butyl) are disclosed as intermediates in the synthesis of the corresponding acetates. Only the latter are said to be fragrance materials.

In U.S. Pat. No. 3,769,330 1-ethyl-2-(C4-alkyl) cyclohexanols (C4=n.butyl, isobutyl, sec.butyl or tert.butyl) are disclosed as fragrance materials with a woody odour.

It has now been found that 3-alkylcycloalkanols of the formula I below are valuable fragrance materials with strong floral odours with citrus and/or rhubarb and sometimes herbal notes. The floral odour is particularly characterized by its overriding muguet character. The citrus notes are sometimes reminiscent of grapefruit.

SUMMARY OF THE INVENTION

In one aspect the invention thus provides a perurne comprising fragrance materials known in the art and at least one alcohol according to Formula I:

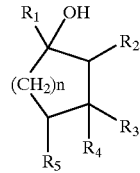

Formula I wherein R1 represents hydrogen or a methyl, ethyl or propyl group; R2, R4 and R5 independently represent hydrogen or a methyl group; R3 represents a saturated hydrocarbon group with 4–8 carbon atoms, provided that the first carbon atom of this hydrocarbon group is not a tertiary carbon atom; n represents the numbers 1, 2 and 3.

The compounds in which R1 is methyl, ethyl or propyl are novel per se.

Preferably R1 is hydrogen or a methyl or ethyl group, more preferably it is methyl or ethyl.

Preferably R5 is hydrogen, more preferably R2 and R5 are both hydrogen, most preferably R2, R4 and R5 are all hydrogen.

Preferably R3 is an alkyl group which comprises at least one secondary carbon atom or a cyclopentyl, cyclohexyl or cycloheptyl group; more preferably, if R3 is an alkyl group, C-atom 2 or 3 (counted from the C-atom attached to the ring) is a secondary carbon atom. Most preferably R3 is cyclohexyl, isobutyl or isoamyl.

Preferably n is 2 or 3, more preferably n is 2.

Thus, the invention provides perfumes and perfumed products comprising the alcohols according to Formula I. Furthermore, the invention provides a process for imparting a floral odour note, more particularly a muguet-type odour note, to perfumes and products specified above.

The alcohols according, to the invention may be used as such in a wide variety of products, or they may be used as components of a perfume to contribute their floral odour. This odour note does not necessarily need to be the strongest or predominant odour note in the perfume or the final perfumed product, but it clearly contributes to the overall odour of such perfume or perfumed product.

For the purposes of this invention a perfume is defined as a mixture of fragrance materials, if desired mixed with or dissoved in a suitable solvent or mixed with a solid substrate, which is used to impart a desired odour to the skin and/or any product for which an agreeable odour is indispensible or desirable. The alcohols according to the invention and the perfumes containing them are particularly suitable for use in e.g.: fabric washing powders, washing liquids, fabric softeners and other fabric care products; soaps, bath and shower gels, shampoos, hair conditioners and other personal cleansing products; cosmetic products such as creams, ointments, toilet waters, products for pre-shave or aftershave use, skin and other lotions, talcum powders, body deodorants and antiperspirants.

Other fragrance materials known in the art which can be advantageously combined with an alcohol according to the invention in a perfume, for example, natural products such as extracts, essential oils, absolutes, resinoids, resins, concretes etc., but also synthetic materials such as hydrocarbons, alcohols, aldehydes, ketones, ethers, acids, esters, acetals, ketals, nitriles, etc., including saturated and unsaturated compounds, aliphatic, carbocyclic and heterocyclic compounds.

Such fragrance materials are mentioned, for example, in S. Arctander, Perfume and Flavor Chemicals (Montclair, N.J., 1969), in S. Arctander, Perfume and Flavor Materials of Natural Origin (Elizabeth, N.J., 1960) and in "Flavor and Fragrance Materials—1991" Allured Publishing Co. Wheaton, Ill. USA.

Examples of fragrance materials which can be used in combination with an alcohol according to the invention are: geraniol, geranyl acetate, linalol, linalyl acetate, tetrahydrolinalol, citronellol, citronellyl acetate, dihydromyrcenol, dihydrornyrcenyll acetate, tetrahydromyrcenol, terpineol, terpinyl acetate, nopol, nopyl acetate., 2-phenylethanol, 2-phenylethyl acetate, benzyl alcohol, benzyl acetate, benzyl salicylate, styrallyl acetate, benzyl benzoate, amyl salicylate, dimethylbenzyl-carbinol, trichloromethylphenylcarbinyl acetate, p-tert-butylcyclohexyl acetate, isononyl acetate, vetiveryl acetate, vetiverol, α-hexylcinnamaldehyde, 2-methyl-3-(p-tert-butylphenyl)propanal, 2-methyl-3-(p-isopropylphenyl) propanal, 3-(p-tert-butylphenyl)propanal, 2,4-dimethyl-3-cyclohexenylcarboxaldehyde, tricyclodecenyl acetate, tricyclodecenyl propionate, 4-(4-hydroxy-4-methylpentyl)-3-cyclohexenecarboxaldehyde, 4-(4methyl-3-pentenyl)-3-cyclohextenecarboxaldehyde, 4-acetoxy-3-pentyl-tetrahydropyran, 3-carboxymethyl-2-pentylcyclopentane, 2-n-heptylcyclopentanone, 3-methyl2-pentyl-2-cyclopentenone, n-decanal, n-dodecanal, 9-decen-1-ol, phenoxyethyl isobutyrate, phenylacetaldehyde dimethylacetal, phenylacetaldehyde diethylacetal, seranyl nitrile, citronellyl nitrile, cedryl acetate, 3-isocamphylcyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indane muslks, tetralin musks, isochroman musks, macrocyclic ketones, macrolactone musks, ethylene brassylate.

Solvents which can be used for perfumes which contain alcohols according to the invention are, for example: ethanol, isopropanol, diethyleneglycol monoethyl ether, dipropylene glycol, diethyl phthalate, triethyl citrate, isopropyl myristate, etc.

The compounds according to the invention may be prepared according to procedures known in the art. The cyclohexanols in which R1 and R4 are hydrogen may be prepared by catalytic hydrogenation of the corresponding phenols such as is known for various 4-alkylcyclohexanols and is described e.g. in EP 0 005 196 and in U.S. Pat. No. 4,400,545, either directly or via the corresponding ketone. If the ketone is obtained, R1 may be introduced with a suitable organometallic reagent such as a Grignard reagent, see U.S. Pat. No. 4,400,545 and U.S. Pat. No. 4,277,618. An alternative procedure for the catalytic reduction of various substituted phenols is described in GB 2 016 449.

Alternatively, 2-cyclopentenone, 2-cyclohexenone or 2-cycloheptenone may be used as the starting material, suitably substituted with methyl group(s) if R2, and/or R4 and/or R5 are methyl. R3 may be introduced therein through a 1,4 conjugate addition reaction with a suitable organometallic compound such as a Grignard reagent in the presence of a copper salt, while trapping out the substituted ketone as a silyl enol ehter if desired. Thereafter, R1 may be introduced again through reaction with a suitable organometallic reagent such as a Grignard reagent or an alkyl-lithium reagent.

The alcohols according to the invention are generally obtained as mixtures of cis and trans isomers (OH and R3 on the same side or opposite sides of the ring respectively), the cis/trans ratio being dependent on the synthesis procedure. Generally the odours of both isomers are different and the isomers may be separated by procedures known in the art such as column chromatography, fractional distillation and gas chromatography. The isomers may be used separately as fragrance materials or the isomer mixtures obtained from the synthetic procedure may be used as such, depending on which particular odour character or mixture of odour characters is preferred for a particular application. Also, the alcohols according to the invention exist in various stereoisomeric forms. They are obtained by the synthetic procedures described above as racemic mixtures, which may be separated into the various stereoisomers by procedures known in the art, particularly by gas chromatography using chiral columns. Therefore, the invention provides the alcohols as cis/trans and stereoisomeric mixtures as well as the various cis and trans and stereoisomers separately and includes the use of these separate isomers as fragrance materials.

The quantities in which an alcohol according to the invention can be used in perfumes or in products to be perfumed may vary within wide limits and depend, inter alia, on the nature of the product, on the nature and the quantity of the other components of the perfume in which the compound is used and on the olfactive effect desired. It is therefore only possible to specify wide limits, which, however, provide sufficient information for the specialist in the art to be able to use the alcohols according to the invention for his specific purpose. In perfumes an amount of 0.01% by weight or more of an alcohol according to the invention will generally have a clearly perceptible olfactive effect. Preferably the amount is 0.1% by weight or more, more preferably at least 1%. Generally it will be less than 80% by weight. The amount of alcohol according to the invention in a product will generally be at least 10 ppm by weight, preferably at least 100 ppm, more preferably at least 1000 pp. However, levels of up to 20% by weight may be used in particular cases, depending on the product to be perfumed.

The invention will be further described, by way of illustration, in the following examples.

EXAMPLE 1

Preparation of 1-methyl-3-(2-methypropyl) cyclohexan-1-ol

Isobutyl magnesium bromide was prepared from magnesium metal (72 g, 3.0 mol) in 500 ml diethylether by dropwise addition of a solution of 1-bromo-2-methylpropane (411 g, 3.0 mol) in 400 ml ether. The Grinard reagent was cooled to −20° C. and a catalytic amount (29 g, 0.015 mol) of copper iodide was added. The temperature was further reduced to 40° C. and a solution of 2-cyclohexen-1-one (144 g, 1.5 mol) in 300 ml ether was added dropwise over 60 minutes while the reaction mixture was stirred. After the addition was complete the reaction mixture was allowed to warm to 0° C. The reaction mixture was quenched through slow addition of 700 ml of water while the temperature was kept below 10° C. through cooling. 10% Hydrochloric acid (150 ml) was added and any remaining solid was filtered off through celite, leaving two yellow phases. The organic phase was separated and washed successively with 10% hydrochloric acid (1000 ml), water (500 ml), and saturated sodium bicarbonate solution (500 ml). The solvent was removed by evaporation in vacuo, leaving 199.7 g of crude product, which contained about 80% by weight (as determined by internal standard gas chromatography analysis) of 3-(2-methylpropyl) cyclohexanone (70% yield).

The crude was distilled under reduced pressure using a 0.5 m Sulzer packed column and 86 g (38% yield based on starting ketone) of pure product was obtained at a head temperature of 56–60° C. and pressure of 0.05 kPa.

A solution of 62.7 g (0.407 mol) of the distilled ketone in 200 ml ether was added dropwise to a stirred solution of 0.6 mol methyl magnesium iodide in 200 ml ether at such a rate that the reaction mixture was allowed gradually to reach and then maintain a steady reflux. When the addition was complete heat was applied to maintain reflux for a further 30 minutes. Thereafter the reaction mixture was quenched with 1.01 of water and the resulting precipitate in the aqueous phase dissolved by the addition of saturated aqueous ammonium chloride (1.01). The organic phase was separated, washed, dried and the solvent was removed in vacuo. The crude consisted of a mixture of trans and cis 1-methyl-3-(2-methylpropyl)cyclohexan-1-ol in a ratio of 2:1. It could be purified by distillation under reduced pressure to obtain a mixture of about the same isomer distribution. Alternatively it could be separated into the cis and trans isomers by column chromatography over silica (200 g for 4 g of crude) using a mixture of diethyl ether and pentane (1.5 v/v ratio) as the eluent. It could also be separated into the isomers by fractional distillation under reduced pressure over a 1 m Sulzer column using a reflux: take off ratio of 10:1. Thus, 217 g of crude yields 102 g (>94% pure on gc) of the trans isomer (head temperature 69° C. at 0.04 kPa) and 50 g (>97% pure on gc) of the cis isomer (62° C. at 0.01 kPa) and 43 g of an intermediate fraction consisting of a mixture of the two isomers.

Trans: (assuming chair conformation with the isobutyl being equatorial then OH is axial and Me is equatorial) white crystalline solid, mp=39–40° C.;

$C^{13}$ NMR: 21.71 ($CH_2$), 22.78 ($CH_3$), 23.00 ($CH_3$), 24.63 (CH), 30.45 (CH), 31.76 ($CH_3$), 32.48 ($CH_2$), 38.74 ($CH_2$), 46.01 ($CH_2$), 46.84 ($CH_2$), 69.95 (C);

$H^1$ NMR: 0.68 (1H,m), 0.82 (3H,d,J=6.6 Hz), 0.83 (3H, d,J=6.6 Hz), 0.90 (1H,m), 0.99 (2H,m), 1.17 (3H,s), 1.24 (1H,m), 1.33 (1H,s,OH), 1.60 (7H,m).

Cis: (assuming chair conformation with the isobutyl being equatorial then OH is equatorial and Me is axial) colourless liquid;

$C^{13}$ NMR: 22.72 ($CH_3$), 22.80 ($CH_3$), 23.74 ($CH_2$), 24.69 (CH), 26.00 ($CH_3$), 32.82 ($CH_2$), 33.10 (CH), 40.60 ($CH_2$), 46.69 ($CH_2$), 47.66 ($CH_2$), 71.34 (C);

$H^1$ NMR: 0.72 (1H,m), 0.81 (3H,d,J=6.6 Hz), 0.83 (3H, d,J=6.6 Hz), 1.05 (3H,m), 1.19 (3H,s), 1.28 (2H,m), 1.43 (2H,m,OH), 1.63 (5H,m).

The cis/trans mixture has a strong floral odour of the muguet and lilac type with herbal, pine and citrus notes. The trans and cis isomers both have floral (muguet-type) odours although the trans has more fruity and rhubarb notes, whereas the cis has more herbal and pine notes.

The following gc olfactometry odour evaluation was performed on the trans and cis isomers.

On a chiral gc column[1] 1-methyl-3-(2-methylpropyl) cyclohexan-1-ol appeared as four peaks. Gc olfactometry was performed using 5% solutions of the isolated trans- and cis- isomers. This meant that each isomer was smelt at the same concentration thus making it easier to compare relative odour strengths.

| Geometric Isomer | Enantiomer | Retention Time | % rpa | Odour |
|---|---|---|---|---|
| trans- | 1 | 25.04 | 33.0 | strong, citrus, grapefruit, rhubarb, floral |
| trans- | 2 | 25.89 | 33.3 | strong, floral, |
| cis- | 1 | 27.60 | 14.5 | weak, citrust, grapefruit |
| cis- | 2 | 27.87 | 14.9 | strong, floral, muguet |

[1]Column: CP-Chirasil-Dex CB, dimensions: 25 m * 0.25 mm * 0.25 μm, linear velocity: 17.15 cm/sec, temperature prog: 70°3°/min 220° (30 min) split flow:ratio 190:1.

EXAMPLES 2–8

The following compounds were prepared following the procedure described in EXAMPLE 1. The odour evaluation is given for each compound:

1-Ethyl-3-(2-methylpropyl)cyclohexan-1-ol (trans): muguet, freesia, fruity, citrus.

1-Ethyl-3-(2-methylpropyl)cyclohexan-1-ol (cis): muguet, citrus, rhubarb, terpineol.

1-Methyl-3-cyclohexylcyclohexan-1-ol (trans): strong, muguet, citrus, rhubarb.

1-Methyl-3-cyclohexylcyclohexan-1-ol (cis): weak, floral, woody.

1,2-Dimethyl-3-(2-methylpropyl)cyclohexan-1-ol (mixture): muguet, slightly terpenic.

1-Methyl-3-(3-methylbutyl)cyclohexan-1-ol (mixture): muguet, rhubarb, grapefruit.

1,3-Dimethyl-3-(2-methylpropyl)cyclohexan-1-ol (mixture). muguet, rhubarb.

EXAMPLES 9–11

The following compounds were obtained following the procedure of the first step of EXAMPLE 1 followed by reduction of the ketone:

3-(2-Methylpropyl)cyclohexan-1-ol (mixture): floral, herbal, slightly woody.

3-(3-Methylbutyl)cyclohexan-1-ol (trans): strong, fatty, grapefruit, rhubarb, muguet, rose, citronellal.

3-(3-Methylbutyl)cyclohexan-1-ol (cis): weak, very fatty, floral, nutty.

EXAMPLE 12

Preparation of 1-methyl-3-(2-methylpropyl) cyclopentan-1-ol

The isobutyl magnesium bromide was prepared as described in EXAMPLE 1, using THF as the solvent. 0.15 Mol of this Grignard reagent in 150 ml THF was cooled to −10° C. and 35.8 g (0.2 mol) of hexamethylphosphoramide added. The resulting yellow solution was cooled to −50° C., 0.95 g of copper iodide added and the solution further cooled to −70° C. At this temperature a solution of trimethylchlorosilane (21.7 g, 0.2 mole) and 2-cyclopenten-1-one (8.20 g, 0.1 mol) in THF (50 ml) was added dropwise. When the addition was complete the reaction mixture was allowed to warm to ambient. Triethylamine (20.2 g, 0.2 mole) and pH 7 buffer (5.0 ml) were added successively, which produced a thick white precipitate. Pentane (100 ml) was added and the mixture was stirred. The precipitate was filtered off, the filtrate was washed with water and dried over magnesium sulphate. The solvent was removed in vacuo and a crude yield of 18.5 g of 3-(2-methylpropyl)cyclopent-1-en-1-yl trimethylsilyl ether was obtained.

A 1.6M ethereal methyllithium solution (46 ml) was added dropwise to a stirred solution of the silyl enol ether (7.86 g, 0.037 mol) in diethylether at a temperature of 0° C. When addition was complete the reaction mixture was allowed to warm to ambient temperature and stirred for 3 hours. GC analysis showed the reaction mixture to contain 53% of 3-methylpropyl)cyclopentan-1-one and 33% of 1-methyl-3-(2-methylpropyl)cyclopentan-1-ol. The reaction mixture was quenched with 10% hydrochloric acid (25 ml). The two phases were separated, the aqueous phase was extracted with ether and the combined organic phases were washed with water and bicarbonate solution and dried over magnesium sulphate. The solvent was evaporated in vacuo to yield 4.63 g of crude product. A methyl Grignard reaction was performed on this crude to convert the remaining ketone into the desired alcohol. The alcohol (isomer mixture) had a strong muguet odour.

EXAMPLE 13

1-Methyl-3-(2-methylpropyl)cycloheptan-1-ol was prepared following the procedure described in EXAMPLE 12 starting from 2-cyclohepten-1-one. The compound had a strong muguet odour with rhubarb notes.

EXAMPLE 14

A perfume composition of the floral (lilac) type was prepared according to the following recipe:

| | |
|---|---|
| α-Terpineol | 12 parts |
| Jasmine absolue 50% | 4 parts |
| Heliotropin, 20% in DPG | 2 parts |
| Traseolide* | 1 part |
| Peru Balsam | 1 part |
| 1-methyl-3-(2-methylpropyl)cyclohexan-1-ol (Isomer mixture obtained in EXAMPLE 1) | 2 parts. |

*Indane musk marketed by Quest International, Ashford Kent, U.K.

The addition of the alcohol according to the invention enhances the floral character and diminishes the harsh notes of terpineol.

What is claimed is:

1. In a perfume composition comprising a mixture of fragrance materials, the improvement which comprises including, in said composition, at least one alcohol according to Formula I:

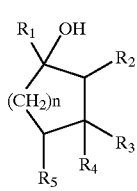

Formula I wherein R1 represents a methyl, ethyl or propyl group; R2, R4 and R5 independently represent hydrogen or a methyl group; R3 represents a saturated hydrocarbon group with 4–8 carbon atoms, provided that the first carbon atom of this hydrocarbon group is not a tertiary carbon atom, and n represents the numbers 1, 2 and 3, said alcohol providing a muguet-type odor note to said composition.

2. A perfume according to claim 1 wherein R1 is methyl or ethyl.

3. A perfume according to claim 1 wherein R5 is hydrogen.

4. A perfume according to claim 1 wherein R3 is an alkyl group which comprises at least one secondary carbon atom or a cyclopentyl, cyclohexyl or cycloheptyl group.

5. A perfume according to claim 4 wherein R3 is cyclohexyl, isobutyl or isoamyl.

6. A perfume according to claim 1 wherein the alcohol is 1-methyl-3(2-methylpropyl)cyclohexan-1-ol.

7. A perfume composition comprising a mixture of fragrance materials and 3(3-methylbutyl)cyclohexan-1-ol.

8. A perfume according to claim 1 or claim 7 wherein the alcohol is present in an amount of at least 0.01% by weight.

9. A process for imparting a floral odour note to products to be perfumed, comprising the step of incorporating in the product a perfume according to claim 1 or claim 7.

10. A process according to claim 9 wherein the product to be perfumed is chosen from the group consisting of: fabric washing powders, washing liquids, fabric softeners, soaps, bath and shower gels, shampoos, hair conditioners, cosmetic creams, ointments, toilet waters, products for preshave or aftershave use, skin lotions, talcum powders, body deodorants and antiperspirants.

11. 3-Alkylcycloalkanol according to the formula I:

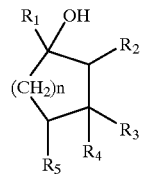

Formula I wherein R1 represents a methyl, ethyl or propyl group; R2, R4 and R5 independently represent hydrogen or a methyl group; R3 represents a saturated hydrocarbon group with 4–8 carbon atoms, provided that the first carbon atom of this hydrocarbon group is not a tertiary carbon atom and n represents the numbers 1, 2 and 3.

12. 3-Alkylcycloalkanols according to claim 11 wherein R1 is methyl or ethyl.

13. 3-Alkylcycloalkanols according to claim 11 wherein R5 is hydrogen.

14. 3-Alkylcycloalkanols according to claim 11 wherein R3 is an alkyl group which comprises at least one secondary carbon atom or a cyclopentyl, cyclohexyl or cycloheptyl group.

15. 3-Alkylcycloalkanols according to claim 14 wherein R3 is cyclohexyl, isobutyl or isoamyl.

16. 1-Methyl-3-(2-methylpropyl)cyclohexan-1-ol.

* * * * *